United States Patent [19]

Nonomura et al.

[11] Patent Number: 5,962,717
[45] Date of Patent: Oct. 5, 1999

[54] PLANT MICRONUTRIENT CHELATING SURFACTANT COMPOUNDS

[75] Inventors: Arthur M. Nonomura, Boxborough, Mass.; Barry A. Cullen, Lyndeborough; Joseph J. Crudden, Hudson, both of N.H.; John J. Nishio, Laramie, Wyo.

[73] Assignee: Hampshire Chemical Corp., Lexington, Mass.

[21] Appl. No.: 09/265,268

[22] Filed: Mar. 9, 1999

Related U.S. Application Data

[62] Division of application No. 08/978,234, Nov. 25, 1997.

[51] Int. Cl.[6] .............................. C07F 3/06; C07F 15/06; C07F 13/00
[52] U.S. Cl. ............................ 556/50; 556/134; 556/148; 71/27; 71/DIG. 2

[58] Field of Search ............................ 556/134, 50, 148; 71/27, DIG. 2

[56] References Cited

U.S. PATENT DOCUMENTS

| 4,741,831 | 5/1988 | Grinstead | 210/638 |
| 4,808,385 | 2/1989 | Grinstead | 423/226 |
| 5,250,728 | 10/1993 | Parker et al. | 562/565 |
| 5,284,972 | 2/1994 | Parker et al. | 562/565 |

*Primary Examiner*—Porfirio Nazario-Gonzalez
*Attorney, Agent, or Firm*—Nields, Lemack & Dingman

[57] ABSTRACT

Plant micronutrient compounds comprising N-acyl ED3A or salts thereof. The N-acyl ED3A derivatives chelate various trace metals, including iron, copper, zinc, manganese, cobalt and nickel.

3 Claims, No Drawings

PLANT MICRONUTRIENT CHELATING SURFACTANT COMPOUNDS

This application is a Divisional of U.S. Ser. No. 08/978,234 filed on Nov. 25, 1997.

BACKGROUND OF THE INVENTION

Ethylenediaminetriacetic acid (ED3A) and its salts (such as ED3ANa$_3$) have applications in the field of chelating chemistry and may be used as a starting material in the preparation of strong chelating polymers, oil soluble chelants, surfactants and others. Conventional routes for the synthesis of ethylenediaminetriacetic acid were achieved via its N-benzyl derivative, which was subsequently hydrolyzed in alkaline solutions to ED3ANa$_3$, thus avoiding cyclization to its 2-oxo-1,4-piperazinediacctic acid (3KP) derivative.

U.S. Pat. No. 5,250,728, the disclosure of which is hereby incorporated by reference, discloses a simple process for the synthesis of ED3A or its salts in high yield. Specifically, a salt of N,N'-ethylenediaminediacetic acid (ED2AH$_2$) is condensed with stoichiometric amounts, preferably slight molar excesses of formaldehyde at a temperature between 0° and 110° C., preferably 0° to 65° C. and pH's greater than 7.0, to form a stable 5-membered ring intermediate. The addition of a cyanide source, such as gaseous or liquid hydrogen cyanide, aqueous solutions of hydrogen cyanide or alkali metal cyanide, in stoichiometric amounts or in a slight molar excess, across this cyclic material at temperatures between 0° and 110° C., preferably between 0° and 65° C., forms ethylenediamine N,N'-diacetic acid-N'-cyanomethyl or salts thereof (mononitrile-diacid). The nitrile in aqueous solutions may be spontaneously cyclized in the presence of less than 3.0 moles base: mole ED2AH$_2$, the base including alkali metal or alkaline earth metal hydroxides, to form 2-oxo-1,4-piperazinediacetic acid (3KP) or salts thereof, which is the desired cyclic intermediate. In the presence of excess base, salts of ED3A are formed in excellent yield and purity. This patent also discloses an alternative embodiment in which the starting material is ED2AH$_a$X$_b$, where X is a base cation, e.g., an alkali or alkaline earth metal, a is 1 to 2, and b is 0 to 1 in aqueous solutions. The reaction mixture also can be acidified to ensure complete formation of carboxymethyl-2-oxopiperazine (the lactam) prior to the reaction. Formaldehyde is added, essentially resulting in the hydroxymethyl derivative. Upon the addition of a cyanide source, 1-cyanomethyl-4-carboxymethyl-3-ketopiperazine (mononitrile monoacid) or a salt thereof is formed. In place of CH$_2$O and a cyanide source, HOCH$_2$CN, which is the reaction product of formaldehyde and cyanide, may also be employed in this method. Upon the addition of any suitable base or acid, this material may be hydrolyzed to 3KP. The addition of a base will open this ring structure to form the salt of ED3A.

U.S. Pat. No. 5,284,972, the disclosure of which is hereby incorporated by reference, discloses N-acyl ED3A derivatives and a process for producing the same. The production of N-acyl derivatives of ethylenediaminetriacetic acid can be accomplished according to the following general reaction scheme:

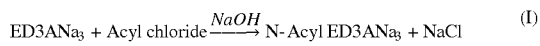

$$\text{ED3ANa}_3 + \text{Acyl chloride} \xrightarrow{NaOH} \text{N-Acyl ED3ANa}_3 + \text{NaCl} \qquad (I)$$

The starting ED3A derivative can be the acid itself, or suitable salts thereof, such as alkali metal and alkaline earth metal salts, preferably sodium or potassium salts.

N-Acyl ED3A salts are mild, biodegradable anionic surfactants. Suitable acyl groups can be of various acyl chain length and include lauroyl (C$_{12}$), myristoyl (C$_{14}$), cocoyl (C$_{8-18}$), palmitoyl (C$_{16}$), pelargoyl (C$_9$) and oleoyl (C$_{18}$).

Agricultural formulations often contain secondary nutrients or micronutrients, as most any nutrient deficiency will lead to loss of plant productivity. Plants deficient in a particular element will exhibit symptoms that usually reflect that specific elemental limitation. Common symptoms of nutrient deficiency are chlorosis (the yellowing of leaves) and necrosis (dead area of leaves); nitrogen deficiency causes a general yellowing of old leaves, whereas iron deficiency causes chlorosis in new shoots. A zinc deficiency will cause "little leaf"; a boron deficiency will cause bronzing and loss of meristemiatic growth; a phosphorus deficiency will cause leaves to turn purple, etc.

Plant nutrients contained in agricultural formulations are metals, usually in the form of chelated metal complexes. EDTA and HEEDTA are the most commonly used chelating agents and the most frequently supplemented micronutrient metals are iron, copper, manganese and zinc. Several other metals are also used as micronutrients in formulations, including boron and molybdenum. Secondary nutrients are sulfur, calcium and magnesium. Primary nutrients are nitrogen, phosphorus and potassium.

None of the prior art chelating agents is also a surfactant. It would be desirable to provide a trace mineral chelating agent that has surfactant properties.

SUMMARY OF THE INVENTION

The problems of the prior art have been overcome by the present invention, which provides novel plant micronutrient compounds comprising N-acyl ED3A or salts thereof. The N-acyl ED3A derivatives chelate various trace metals, including iron, copper, zinc, manganese, cobalt and nickel.

DETAILED DESCRIPTION OF THE INVENTION

Ethylenediaminetriacetic acid and salts thereof can be prepared as disclosed in U.S. Pat. No. 5,250,728, or by other conventional means. Similarly, N-acyl ethylenediaminetriacetic acid and salts thereof can be prepared as disclosed in U.S. Pat. No. 5,250,728, which is hereby incorporated by reference.

Suitable acyl groups for the starting N-acyl derivative of ethylenediaminetriacetic acid ("ED3A") are straight or branched aliphatic or aromatic groups containing from 1 to 40, preferably from 8 to 22, most preferably 8–18 carbon atoms, preferably acyl groups that are carboxylic acid derivatives. Examples of preferred acyl groups are pentanoyl, hexanoyl, heptanoyl, octanoyl, nananoyl, decanoyl, lauroyl, myristoyl, palmitoyl, oleoyl, stearoyl, nonanoyl, neopentanoyl, neoheptanoyl, neodecanoyl, palmitoyl, pelargoyl, iso-octanoyl, iso-nananoyl, isotridecanoyl, benzoyl and naphthoyl. Lauroyl, myristoyl, cocoyl, pelargoyl and oleoyl ethylenediaminetriacetic acid are particular preferred, with the lauroyl derivative being most preferred. The particular identity of the acyl group will depend in part upon the desired solubility of the micronutrient compounds of the present invention. For example, paraffin oil is commonly utilized as a carrier for foliar application of active moieties, therefore a micronutrient compound having a long fatty acid chain available would be most appropriate for its high degree of solubility in oils. On the other hand, with a surfactant/spreader such as SILWET® 408 in an aqueous solution, shorter chain acyl groups such as $C_{10}$ or lower carbon chains such as pelargoyl ethylenediaminetriacetic acid, would be appropriate for enhancement of wetting and penetration into foliage.

The N-acyl ED3A starting material is preferably used in the form of its salt, most preferably its alkali metal salt, particularly sodium or potassium. The potassium salt is particularly preferred, since potassium can contribute to plant nutrition. Ammonium or aminoalcohol salts also can be used. Where the ED3A acid or the N-acyl ED3A acid is produced, it can be readily converted into a salt by partial or complete neutralization of the acid with the appropriate base. Similarly, the acid also can be produced from the corresponding ED3A salts or N-acyl ED3A salts by neutralization with a quantitative amount of acid.

In order to produce the trace metal chelating surfactant of the present invention, the trace metal, such as in the form of its acetate salt, is dissolved in an aqueous solution of the salt of N-acyl ED3A or ED3A at 50–80° C. or the metal powder or metal oxide is dissolved over time into N-acyl ED3A acid or ED3A acid at approximately 80° C. Suitable salts of the metal depend upon the particular metal of concern. Acetate salts are preferred because acetate is known to sequester multivalent ions such as copper. Examples of other suitable salts include cupric sulfate, cupric chloride, cupric nitrate, zinc chloride, zinc bromide, zinc nitrate, zinc undecylenate, ammonium nickel sulfate, potassium permanganate, manganese chloride, manganese sulfate, cobalt chloride, cobalt nitrate, cobalt thiocyanate, cobalt sulfate, ferric ammonium sulfate, ferric citrate, ferric sulfate, ferric tartrate, ferric pyrophosphate, ferric phosphate, ferric nitrate, ferric fluoride, ferric ammonium citrate, ferrous salts, ferrocenes, sodium molybdate and borax. A mixture of salts also may be utilized to manufacture the trace mineral plant formulation of the present invention.

Although molybdenum and boron are essential plant micronutrients, they do not react with N-acyl ED3A. Nevertheless, the N-acyl ED3A is useful for its surfactancy and solutions thereof can be made with these micronutrients.

The amount of metal should be in a ratio to the ED3A or N-acyl ED3A of about 1:3.5; lower ratios (such as 1:2) do not completely dissolve due to lack of sufficient chelation. Sonication is preferably used to enhance the process. Suitable and preferred ranges of micronutrients in the plant nutrient formulations are set forth below:

| Micronutrient | Range (ppb) | Preferred Range (ppb) |
| --- | --- | --- |
| Mn | 0.001–50,000 | 5–250 |
| Zn | 0.0001–200,000 | 0.25–25 |
| Cu | 0.0001–100,000 | 0.1–15 |
| Fe | 0.01–200,000 | 200–2,000 |
| Ni | 0.0001–200 | 0.001–0.05 |
| Co | 0.001–500 | 0.1–1.0 |

The micronutrient solutions of the present invention can be used effectively in nanomolar concentrations. The solutions may be applied to virtually any variety of plant shoots, roots, seeds, tissues, suspension cultures or thalli. The micronutrients can be applied to all photosynthetic organisms such as flowering plants, including angiosperms and gymnosperms, and cryptograms, including ferns, liverworts, mosses, algae and hornworts. In particular, the compositions and methods of the present invention may be advantageously applied to higher plants, including species having true stems, roots and leaves. Examples of plants which may benefit from the instant compositions include all crop plants such as alfalfa, anise, bach ciao, barley, basil, blueberry, breadfruit, broccoli, brussels sprouts, cabbage, cassava, cauliflower, celery, cereals, cilantro, coffee, corn, cotton, cranberry, cucumber, dill, eggplant, fennel, grape, grain, garlic, kale, leek, legume, lettuce, melon, mint, mustard, melon, oat, onion, parsley, peanut, pepper, potato, saffron, legume, lettuce, millet, parsnip, pea, pepper, peppermint, pumpkin, radish, rice, sesame, sorghum, soy, spinach, squash, stevia, strawberry, sunflower, sweet potato, sugar beet, sugar cane, tea, tobacco, tomato, turnip, wheat, yam, zucchini and the like; pomes and other fruit-bearing plants such as apple, avocado, banana, breadfruit, cherry, citrus, cocoa, fig, guava, macadamia, mango, mangosteen, nut, olive, papaya, passion fruit, pear, pepper, plum, peach and the like; floral plants such as achillea, ageratum, alyssum, anemone, aquilegia, aster, azalea, begonia, bird-of-paradise, bleeding heart, borage, bromeliad, bougainvillea, buddlea, cactus, calendula, camellia, campanula, carex, carnation, celosia, chrysanthemum, clematis, cleome, coleus, cosmos, crocus, croton, cyclamen, dahlia, daffodil, daisy, day lily, delphinium, dianthus, digitalis, dusty miller, euonymus, forget-me-not, fremontia, fuchsia, gardenia, gazania, geranium, gerbera, gesneriad, ginkgo, gladiolus, hibiscus, hydrangea, impatiens, jasmine, lily, lilac, lisianthus, lobelia, marigold, mesembryanthemum, mimulus, myosotis, New Guinea Impatiens, nymphaea, oenothera, oleander, orchid, oxalis, pansy, penstemon, peony, petunia, poinsettia, polemonium, polygonum, poppy, portulaca, primula, ranunculus, rhododendron, rose, salvia, senecio, shooting star, snapdragon, solanum, solidago, stock, ti, torenia, tulip, verbena, vinca, viola, violet, zinnia, and the like; leafy plants such as ficus, fern, hosta, philodendron, and the like, trees such as Abies, birch, cedar, Cornus, cypress, elm, fir, juniper, magnolia, mahogany, maple, oak, palm, Picea, Pinus, Pittossporum, Plantago, poplar, redwood, Salix, sycamore, Taxus, teak, willow, yew, Christmas tree and the like; grasses, such as Kentucky blue grass, bent grass, turf, festuca, pennisetum, phalaris, calamogrostis, elymus, helictotrichon, imperata, molina, carex, miscanthus, panicum and the like; and thalloid plants such as ferns and algae. Algae include seaweeds such as kelp, Eucheuma, laver, nori, kombu and wakame. Other plants which may benefit from application of the compositions and methods of the present invention will be apparent to those skilled in the art.

EXAMPLE 1

Preparation of 10% Sodium Lauroyl ED3A Solution

Sodium hydroxide solution was prepared using ACS grade sodium hydroxide from Fisher Scientific and distilled deionized water.

Lauroyl ED3A (LED3A) acid was dispersed in distilled deionized water and neutralized to pH 6.5 with sodium hydroxide. Neutralization to pH 6.5 required approximately 2 moles of NaOH per mole of LED3A. The concentration of the solution was adjusted to exactly 10% sodium LED3A with distilled deionized water.

EXAMPLE 2

Preparation of Metal Chelate Solutions

A. Preparation of Copper Chelate Solution

A four figure Ohaus GA200 digital balance was used to weigh 0.07671 g of cupric acetate monohydrate (formula weight 199.64) into a clean 20 ml glass vial. The weight was made up to 10.00 g using the sodium LED3A solution of Example 1. The resulting solution was clear blue. Based upon calculations from the formula weight of cupric acetate monohydrate, 2442 ppm copper (atomic weight 63.55) was measured into the solution.

A copper control solution was produced by dissolving an equivalent amount of cupric acetate monohydrate in distilled deionized water. The weight was made up to 10.00 g using distilled deionized water. The clear blue solution contained 2442 ppm copper (atomic weight 63.55).

B. Preparation of Zinc Chelate Solution

Zinc acetate dihydrate (formula weight 219.49) was weighed into a clean 20 ml glass vial. The weight was made up to 10.00 g using the sodium LED3A solution of Example 1. The clear solution contained 2514 ppm zinc (atomic weight 65.39).

A zinc control solution was produced by dissolving an equivalent amount of zinc acetate dihydrate in distilled deionized water. The weight was made up to 10.00 g using distilled deionized water. The clear blue solution contained 2514 ppm zinc.

C. Preparation of Nickel Chelate Solution

Nickel (II) acetate tetrahydrate (formula weight 248.86) was weighed into a clean 20 ml glass vial. The weight was made up to 10.00 g using the sodium LED3A solution of Example 1. The solution contained 2257 ppm nickel (atomic weight 58.69).

A nickel control solution was produced by dissolving an equivalent amount of nickel (II) acetate tetrahydrate in distilled deionized water. The weight was made up to 10.00 g using distilled deionized water. The solution contained 2257 ppm nickel.

D. Preparation of Manganese Chelate Solution

Manganese (II) acetate tetrahydrate (formula weight 245.09) was weighed into a clean 20 ml glass vial. The weight was made up to 10.00 g using the sodium LED3A solution of Example 1. The solution contained 2497 ppm manganese (atomic weight 54.93805).

A manganese control solution was produced by dissolving an equivalent amount of manganese (II) acetate tetrahydrate in distilled deionized water. The weight was made up to 10.00 g using distilled deionized water. The solution contained 2497 ppm manganese.

E. Preparation of Cobalt Chelate Solution

Cobalt acetate tetrahydrate (formula weight 249.08) was weighed into a clean 20 ml glass vial. The weight was made up to 10.00 g using the sodium LED3A solution of Example 1. The solution contained 2266 ppm manganese (atomic weight 58.93320).

A cobalt control solution was produced by dissolving an equivalent amount of cobalt acetate tetrahydrate in distilled deionized water. The weight was made up to 10.00 g using distilled deionized water. The solution contained 2266 ppm cobalt.

F. Preparation of Iron Chelate Solution

Ferric chloride (formula weight 162.22) was weighed into a clean 20 ml glass vial. The weight was made up to 10.00 g using the sodium LED3A solution of Example 1. The clear brown solution contained 2148 ppm iron (atomic weight 55.847).

An iron control solution was produced by dissolving an equivalent amount of ferric chloride in distilled deionized water. The weight was made up to 10.00 g using distilled deionized water. The clear brown solution contained 2148 ppm iron.

G. Preparation of Molybdenum Surfactant Solution

Ammonium molybdate (formula weight 196.02) was weighed into a clean 20 ml glass vial. The weight was made up to 10.00 g using the sodium LED3A solution of Example 1. The solution contained 3690 ppm molybdenum (atomic weight 95.94).

A molybdenum control solution was produced by dissolving an equivalent amount of ammonium molybdate in distilled deionized water. The weight was made up to 10.00 g using distilled deionized water. The solution contained 3690 ppm molybdenum.

H. Preparation of Boron Surfactant Solution

Boric acid (formula weight 61.83) was weighed into a clean 20 ml glass vial. The weight was made up to 10.00 g using the sodium LED3A solution of Example 1. The solution contained 415.4 ppm boron (atomic weight 10.811).

A boron control solution was produced by dissolving an equivalent amount of boric acid in distilled deionized water. The weight was made up to 10.00 g using distilled deionized water. The solution contained 415.4 ppm boron.

EXAMPLE 3

Wheat plants cv. Geneva were hydroponically cultured in an environmentally controlled growth chamber in the laboratory of John Nishio at the University of Wyoming, Laramie, Wyo. The light:dark photoperiod was set at 16:8 h. The temperature was 23° C. during the light period and 19° C. at night with 60% to 70% relative humidity. Plants were illuminated with 330 $\mu mol(m^{-2})(s^{-1})$ photosynthetically active radiation.

Wheat plants were germinated on acid-washed sand and allowed to grow for 12 days. The wheat plants were, thereafter, transplanted into hydroponic culture with distilled water as the medium. Control plants were cultured in black 13.5 liter buckets containing Hoagland solution containing micronutrient-acetates. Treated plants were cultured in a separate set of buckets containing Hoagland solution formulated with lauroyl-ED3A (LED3A) micronutrients. In each bucket, 5 plants were cultured in 0.01× Hoagland solution. Buckets containing 0.05× Hoagland solution each supported 6 plants.

Final concentrations (parts per million) of macronutrient compounds in the 0.01× and 0.05× dilutions of Hoagland solution utilized in the hydroponic culture of wheat follow:

|  | Dilution of Hoagland solution | | |
| --- | --- | --- | --- |
| Compound | 1X | 0.05X | 0.01X |
| $KNO_3$ | 505 ppm | 25.3 ppm | 5.1 ppm |
| $Ca(NO_3)_2$ | 1181 | 59.1 | 11.8 |
| $MgSO_4$ | 493 | 24.5 | 4.9 |
| $KH_2PO_4$ | 136 | 6.8 | 1.4 |

The 0.01× Hoagland solution contained the following nanomolar (nM) and parts per billion (ppb) concentrations of each trace metal:

| Element | Final Concentration (nM) | Final metal ppb |
| --- | --- | --- |
| B | 460 | 5 |
| Cu | 3.1 | 0.2 |
| Fe | 895 | 50 |
| Mn | 90 | 5 |

-continued

| Element | Final Concentration (nM) | Final metal ppb |
|---------|--------------------------|-----------------|
| Mo      | 1                        | 0.1             |
| Zn      | 7.7                      | 0.5             |

The 0.05× Hoagland solution for the hydroponic culture of wheat contained the following parts per billion (ppb) concentrations of each trace metal:

| Element | Final metal ppb |
|---------|-----------------|
| B       | 25              |
| Cu      | 1               |
| Fe      | 250             |
| Mn      | 25              |
| Mo      | 0.5             |
| Zn      | 2.5             |

In all hydroponic cultures, distilled water is the diluent and the hydroponic medium.

After 9 days growth in 0.01× Hoagland solution, the three plants with the longest shoots for each treatment were used for analysis. After 30 days growth in 0.05× Hoagland solution, the 4 plants with the longest shoots were used for analysis.

For the 0.01× Hoagland solution, symptoms of nutrient deficiency were exhibited soon after transfer to hydroponic growth in the micronutrient-acetate solution, whereas symptoms of deficiency in the nmicronutrient solution of the present invention were not apparent. In the 0.05× Hoagland solution, the onset of nutrient deficiency also occurred well before symptoms were visible in the inicronutrient solution of the present invention. This allowed significant dry weight (DW) growth differences to be measured for wheat as follows:

| Treatment | Nutrient | Total DW      |
|-----------|----------|---------------|
| LED3A     | 0.05×    | 2.13 ± 0.57   |
| Control   | 0.05×    | 1.59 ± 0.19   |
| p*        | —        | 0.07          |

*n = 6. Probability determined by two-tailed Student's T-test

The wheat plants grown in the solutions of the present invention exhibited longer shoots and roots, as well as increased biomass accumulation. These results show that the micronutrient solutions of the present invention were much more efficiently utilized by the plants than were the micronutrient-acetates of the prior art. The rapid onset of deficiency occurred because the 0.01× Hoagland solution is not normally used for plant growth. The results show that the present solutions can be used effectively for plant growth at nanomolar concentrations.

After three days in hydroponic culture, shoots of the wheat plants grown in the N-acyl ED3A in 0.01× Hoagland solution were visibly longer than shoots from micronutrient-acetate grown plants. The shoots of the latter exhibited extreme nutrient deficiency showing necrosis at an early stage of the experiment. The symptoms were typical of iron deficiency. In contrast, plants grown in the instant solutions developed chlorosis later and were developing necrosis at the time of harvest. Using 0.05× Hoagland solution allowed for a longer period of growth, and consequently, there were larger differences in biomass accumulation compared to growth in the 0.01× solution.

Wheat plants grown in the 0.05× Hoagland solution developed necrosis also, but not as rapidly. Again, plants became yellow and necrotic, and the symptoms of iron deficiency were evident. Plants grown in the N-acyl ED3A micronutrient solution of the present invention developed nutrient deficiency symptoms well after the controls.

EXAMPLE 4

Sugar beet cv. Monohikari plants were hydroponically cultured in an environmentally controlled growth chamber in the laboratory of John Nishio at the University of Wyoming, Laramie, Wyo. The light:dark photoperiod was set at 16:8 h. The temperature was 23° C. during the light period and 19° C. at night with 60% to 70% relative humidity. Plants were illuminated with 330 $\mu mol(m^{-2})(s^{-1})$ photosynthetically active radiation.

Plants were germinated on acid-washed sand and allowed to grow for 16 days. Sugar beets were thereafter transplanted into hydroponic culture. Control plants were cultured in black 13.5 liter buckets containing 0.1× Hoagland solution containing micronutrient-acetates. Treated plants were cultured in a separate set of buckets containing Hoagland solution formulated with lauroyl-ED3A (LED3A) micronutrients.

Final concentrations (parts per million) of macronutrient compounds in the 0.1× Hoagland solution utilized in the hydroponic culture of sugar beet follow:

| Compound    | 0.1X Hoagland solution |
|-------------|------------------------|
| $KNO_3$     | 50.5 ppm               |
| $Ca(NO_3)_2$| 118.1                  |
| $MgSO_4$    | 49.3                   |
| $KH_2PO_4$  | 13.6                   |

The nutrient solutions contained the following parts per billion (ppb) concentrations of each trace metal:

| Element | Final ppb |
|---------|-----------|
| B       | 50        |
| Cu      | 2         |
| Fe      | 500       |
| Mn      | 50        |
| Mo      | 1         |
| Zn      | 5         |

In all hydroponic cultures, distilled water was the diluent and hydroponic medium.

Forty-tvo days after transfer to the hydroponic 0.1× Hoagland solution, four of the largest sugar beets in each of the treated and control studies were selected for analyses. The LED3A-micronutrients increased the fresh weight (FW) yields of the hydroponically grown sugar beets significantly over the controls as tabulated below:

| Treatment | [Nutrient] | Total FW/plant (g) |
|-----------|------------|--------------------|
| LED3A     | 0.1×       | 32.80 ± 5.56       |
| Control   | 0.1×       | 26.85 ± 2.20       |
| p*        | —          | 0.14               |

*n = 4, probability was measured by a two-way Student's T-test.

Roots and shoots of LED3A-micronutrient grown sugar beets were bigger and the total fresh weight of the plants was larger than the controls showing that the LED3A-micronutrients provided better nutrition and growth than the micronutrient-acetates. Controls exhibited nutrient deficiency well before the LED3A-micronutrient treated plants. On the 42nd day of hydroponic culture, all of the plants and leaves showed yellowing; however, necrotic tissue was present in the older leaves of the control plants at harvest, but there was no necrosis in LED3A-micronutrient at that time.

What is claimed is:
1. Cobalt lauroyl ethylenediaminetriacetic acid.
2. Manganese lauroyl ethylenediaminetriacetic acid.
3. Zinc lauroyl ethylenediaminetriacetic acid.

* * * * *